United States Patent [19]
Ellis et al.

[11] Patent Number: 5,376,099
[45] Date of Patent: Dec. 27, 1994

[54] UNDERCUT DIAMOND SURGICAL BLADE AND METHOD OF USING THE SAME

[75] Inventors: William Ellis, Lafayette, Calif.; Kerry K. Assil, St. Louis, Mo.; William R. Knepshield, Malvern; Kristen S. Fay, Glen Mills, both of Pa.

[73] Assignee: KMI, Inc., West Chester, Pa.

[21] Appl. No.: 139,950

[22] Filed: Oct. 20, 1993

Related U.S. Application Data

[60] Division of Ser. No. 967,800, Oct. 28, 1992, which is a continuation-in-part of Ser. No. 946,868, Sep. 17, 1992.

[51] Int. Cl.$^5$ ............................................. A61B 17/32
[52] U.S. Cl. ..................................... 606/166; 606/167; 606/172
[58] Field of Search ....................... 606/166, 172, 167; 30/357, 351, 353, 346.61, 346.55

[56] References Cited

U.S. PATENT DOCUMENTS

| | | | |
|---|---|---|---|
| 2,049,898 | 8/1936 | Driest | 30/9 |
| 2,649,860 | 8/1953 | Royer | 128/314 |
| 3,945,117 | 3/1976 | Beaver | 30/287 |
| 4,185,634 | 1/1980 | Freedman | 128/314 |
| 4,499,898 | 2/1985 | Knepshield et al. | |
| 4,538,356 | 9/1985 | Knepshield et al. | |
| 4,552,146 | 11/1985 | Jensen et al. | |
| 4,602,630 | 7/1986 | Anis | |
| 4,674,503 | 6/1987 | Peyman et al. | 128/305 |
| 4,691,716 | 9/1987 | Tanne | |
| 4,730,613 | 3/1988 | Gordy | |
| 4,750,489 | 6/1988 | Berkman et al. | |
| 4,768,509 | 9/1988 | Grosvenor et al. | |
| 4,815,218 | 3/1989 | Gordy | |
| 4,898,170 | 2/1990 | Hofmann et al. | |
| 5,222,967 | 6/1993 | Casebeer et al. | |

OTHER PUBLICATIONS

Assil et al., "The Undercut Technique of Radial Keratotomy: A Comparison To The Combined Technique", Department of Ophthalmology, St. Louis University's Anheuser-Busch Eye Institute, St. Louis, Mo.

Codman/MICRA, "Titanium Instruments And Diamond Knives For Ophthalmology", Jan. 1985, Printed in USA, Dist. by Codman, Randolph, Mass., pp. 1–6.

Waring, "Repeated Surgery For Residual Myopia And Hyperopia After Refractive Corneal Surgery", In: Waring G. O. ed. Refractive Keratotomy For Myopia And Astigmatism, St. Louis, Mo., Musby Yearbook Inc., 1991, pp. 641–668.

Bores, "Historical Review And Clinical Results At Radial Keratotomy", In: Binder P.S. ed. International Ophthalmology Clinics Refractive Corneal Surgery: The Correction of Aphahia, Hyperopia And Myopia, Boston, Mass.: Little, Brown and Co., 1983, 23:93–118.

Herbert, "The Diamond Knife–Rather More Than Meets The Eye", Industrial Diamond Review, May 1984.

Article entitled "Thin-Profile Diamond Knife Blade Facilitates RK, Reduced Damage", *Ophthalmology Times*, p. 5 (Oct. 1, 1990).

KOI Trade Literature entitled "Diamond Knife Configurations" (1990).

KOI Trade Literature entitled "KOI Diamond Micrometers" (1991).

CooperVision, KOI Division, Trade Literature entitled "Blade Configurations" (1986).

(List continued on next page.)

*Primary Examiner*—Michael H. Thaler
*Attorney, Agent, or Firm*—Duane, Morris & Heckscher

[57] ABSTRACT

Surgical blades, knives and keratotomy procedures are provided which are capable of severing deep corneal tissue in the optical zone without penetrating the surface of this zone and causing optical glare. The blades of this invention include at least one cutting edge thereon which is shorter than about 0.5 mm and which includes a projecting cutting portion and/or recessed blunt edge to permit primary or secondary incisions beneath the surface of the optical zone.

21 Claims, 4 Drawing Sheets

OTHER PUBLICATIONS

KMI, Inc. Trade Literature entitled "Micrometer Diamond Knives" (1991).

KMI, Inc. Trade Literature entitled "Cataract and General Surgery Diamond Knives" and Micrometer Diamond Surgical Knives (1989).

KMI, Inc. Trade Literature entitled "Ophthalmology Update" (Mar., 1988).

KMI, Inc. Trade Literature entitled "Diamond Surgical Knives" (1988).

CooperVision, KOI Division, Trade Literature entitled "KOI Freehand Diamond Knife" (Copyright 1985).

KMI, Inc. Trade Literature entitled "Multi-purpose KMI Freehand Diamond Knife is Ideal for Most Incisions" (1987).

KMI, Inc. Trade Literature entitled "KMI Surgical Products Introduces a New Concept in Diamond Knives" (1989).

CooperVision, KOI Division, Trade Literature entitled "CooperVision KOI Freehand and Micrometer Adjustable".

"Diamond Knives Designed Specifically for Cutting Corneal Tissue" (1985).

International Facilities Corporation Trade Literature, "Microsurgical Diamond Knife" (undated).

KMI, Inc. Trade Literature, "KMI 'gems'are always in the right setting . . . " (1992).

KMI, Inc. Trade Literature, "Radial and Astigmatic Keratotomy Instruments" (1992).

KMI, Inc. Trade Literature, "Genesis. the Beginning of Safe Keratorefractive Surgery" (1992).

Kmi, Inc. Diamond blade configurations styles 18, 19, 24, 33, 3, 4, and 8, distributed during the 1980's.

Melles, et al., "Effect of Radial Keratotomy Incision Direction on Wound Depth", *Journal of Refractive & Corneal Surgery*, vol. 6, pp. 394–403 (Nov./Dec. 1990).

Buzard, "deepening of Incisions After Radial Keratotomy Using the 'Tickle' Technique", *Journal of Refractive & Corneal Surgery*, vol. 7, pp. 348–355 (Sep./Oct. 1991).

Merlin et al., "Factors That Affect Keratotomy Depth", *Journal of Refractive & Corneal Surgery*, vol. 7, pp. 356–359 (Sep./Oct. 1991).

UNDERCUT DIAMOND SURGICAL BLADE AND METHOD OF USING THE SAME

CROSS REFERENCE TO RELATED APPLICATION

This application is a divisional application of commonly-owned U.S. patent application Ser. No. 07/967,800, filed on Oct. 28, 1992, which in turn is a continuation-in-part application of U.S. patent application Ser. No. 07/946,868, filed on Sep. 17, 1992.

FIELD OF THE INVENTION

This invention is related to surgical knives having controllable extendable blades, and more particularly to gemstone blade configurations having at least one cutting edge which is suitable for radial and astigmatic keratotomy procedures.

BACKGROUND OF THE INVENTION

Radial keratotomy procedures are currently available for myopic patients having about 2-6 diopters of myopia. Such keratorefractive procedures attempt to flatten the cornea with radial incisions which begin paracentral to the cornea center and leave the central optical zone of about 3-4 mm unaffected. Two widely available techniques currently employed are known as the Russian (up hill) and the American (down hill) methods. In the Russian method, the incision is started in the cornea near the limbus and is directed to the edge of the optical zone. In the American technique, the initial incision is made at the optical zone, and then proceeds radially outward toward the limbus. With both procedures, approximately 4-16 radial incisions are made in the cornea. These incisions are designed to reconfigure the cornea so that the light entering the eye tends to focus more accurately on the retina. However, since the corneal thickness varies from patient to patient, and from one region of the cornea to the next, and since the skill level of surgeons varies from one surgeon to to the next, the predictability of keratorefractive surgery has typically been low. The lack of predictability and efficiency are especially true when employing the American style incisions, as these typically yield incisions of variable depth.

Recently, as disclosed in U.S. Pat. No. 4,691,716, studies have shown that the efficacy of radial keratotomy and the final degree of refractive correction is significantly influenced by the depth of the incision. Procedures which produce a relatively shallow cut are known to produce the least amount of correction with the greatest degree of regression. Accordingly, surgeons must be careful to cut fully through approximately 90% of the thickness of the cornea in order to provide effective results. Since the American style incisions do not provide uniform depth (producing shallower incisions centrally), and since the corneal periphery is thicker (0.580-0.600 mm) than the paracentral and central corneal zones (0.500 mm) in most patients, the surgeon must redeepen the peripheral cut in order to provide an incision at 90% of the corneal thickness over its entire length, following American style incisions.

Redeepening the incision presents the formidable risk of puncturing the cornea and creating an entrance bacteria to enter the anterior chamber of the eye with attendant risks of infection and complications. Redeepening the incision also often requires lifting the blade and retracing or reversing the cutting motion. This is a very difficult procedure and can result in penetration into the optical zone, as well as inaccurate retracing of the bottom of the incision. Incisions invading the full thickness of the optical zone are associated with optical glare, since the resulting surface scarring has a different refractive index than the surrounding corneal tissue. While the Russian (up hill) incisions tend to provide uniform depth with resultant greater predictability, they are still fraught with the danger of invading the central optical zone. This is because slight irregular movements of the patient's eye or the surgeon's hand may result in optical zone incisions as the blade approaches the central zone.

Accordingly, there is a present need for knive blades and keratotomy surgical procedures which permit carefully controlled keratorefractive incisions approaching 90% of the thickness of the cornea without risking puncture into the anterior chamber or scarring at the surface of the optical zone.

SUMMARY OF THE INVENTION

The present invention provides surgical knives which are designed for use in surgical procedures, especially delimiting, astigmatic and radial keratotomy, and the like. One group of preferred knives includes an elongated blade having proximal and distal ends and front and back opposing planar surfaces. These blades further include first and second longitudinal sides, which together with the planar surfaces, form generally rectangular blade configurations having an angular transverse distal end. At the distal end of these blades, first and second cutting edges are provided which extend distally from the first and second longitudinal sides of the gemstone to form a sharp apex for piercing into a cornea. The second cutting edge can be shorter than the length of the first cutting edge and can have a cutting depth of significantly less than the thickness of the cornea, about 0.500 mm and preferably less than about 0.350 mm, with a critical minimum established at about 0.120 mm for the cleanest incisions.

Accordingly, these surgical blades permit ophthalmologists to take advantage of the benefits of both the Russian and American radial keratotomy techniques. The initial incision can be performed employing the relatively safe American technique, while the redeepening procedure can be produced employing the Russian method with the second cutting edge. Since the second cutting edge is significantly shorter than the thickness of the cornea in the central corneal region, and a blunt edge is provided proximal to this cutting surface, the redeepening procedure presents no greater risk than that involved with the American technique.

The knives of this embodiment are equipped to provide redeepening procedures without the surgeon lifting the knife. The incision is merely retraced with the second cutting edge, which tends to deepen the incision, while a blunt portion proximal to the second cutting edge prevents intrusion into the optical zone. These features substantially eliminate the risk of corneal puncture, as well as scarring of the superficial optical zone.

In further embodiments of this invention, surgical knives are provided which include the above-described gemstone blades having first and second cutting edges located distally from the longitudinal sides of the blade. The blade is set in a blade holder which is sized to fit within a surgeon's hand and includes a foot portion for contacting and gliding over a peripheral portion of the cornea, while helping to maintain the blade at a selected incision depth. The surgical knife also preferably includes a micrometer for accurately setting the extension of the blade beyond the foot portion of the blade holder.

This invention also provides surgical radial keratotomy procedures which include providing a surgical knife having a primary cutting edge and a second shorter cutting edge having a cutting depth of substantially less than the thickness of the cornea. The blade of the surgical knife is pierced into the cornea tissue with the sharp apex located at the distal tip, and an incision is made radially outward from about the optical zone, cutting toward the limbus. The bottom portion of the incision is then deepened with the second cutting edge of the blade by retracing back toward the optical zone, without puncturing the cornea or significantly optically interfering with the optical zone. The blades of this invention are also useful in post-radial-keratotomy enhancement procedures in which the blade is later reintroduced into the "old tunnels" of the wound and the verticle edge is used to scrape the bottom.

Finally, blade designs are provided by this invention which are capable of "undercutting" the cornea beneath the optical zone at a preferred vertical orientation to provide further flattening of the cornea and for correcting as much as about 6–12 diopters, or more, of myopia. These blade constructions preferably include a recess along the longitudinal side of the blade cutting edge. This recess enables the redeepening incision to penetrate as much as 0.05 mm, or more, beneath the optical zone with potentially dramatic results in keratorefractive correction ability, without the associated problems of glare as no surface scarring occurs. The distal end of the blunt edge is spaced from a distal tip of said blade a distance no greater than a thickness of the corneal tissue, and is located distally beyond the proximal end of the primary cutting surface, so as to assist in minimizing penetration by the blade into the surface tissue of the optical zone.

BRIEF DESCRIPTION OF THE DRAWINGS

The accompanying drawings illustrate preferred embodiments of the invention according the practical application of the principles thereof, and in which.

DETAILED DESCRIPTION OF THE INVENTION

Figure 1:
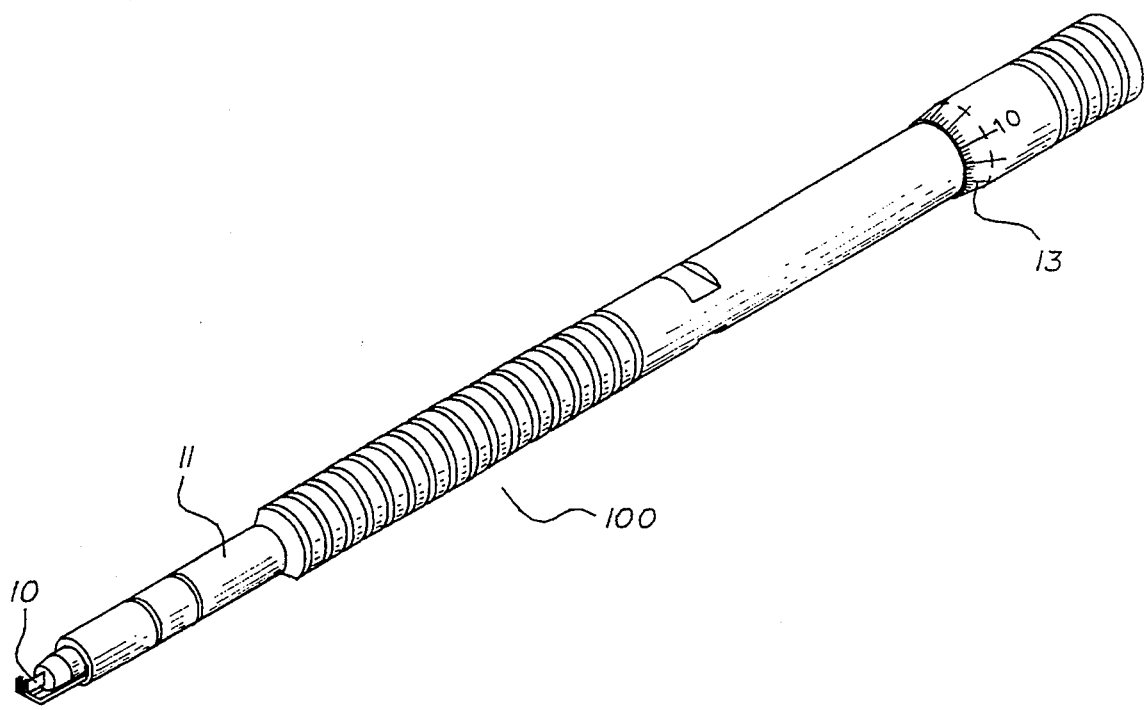
FIG. 1 is a perspective view of a micrometer surgical knife of this invention.
Figure 2:
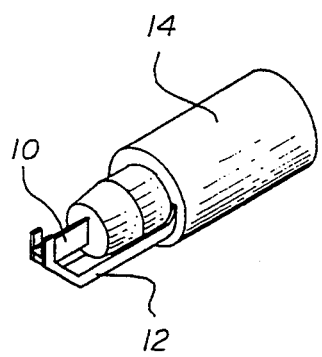
FIG. 2 is a partial perspective, enlarged view of the distal end of the micrometer surgical knife of FIG. 1.

Surgical blades, knives and radial keratotomy procedures are provided by this invention which provide ophthalmologists with equipment and techniques for corrective procedures having high efficacy with minimal risk of complications. Although keratorefractive surgical procedures are disclosed, the surgical blades of this invention can be used for any surgical, or microsurgical application which requires maneuverability and tactile sensitivity.

With reference to the figures, and particularly to FIGS. 1–5 thereof, there is shown a preferred micrometer surgical knife 100 having a blade 10 and a knife body 11. As shown in the enlarged view of FIG. 2, the blade is affixed to the distal end 14 of the knife body 11 and is positioned at a preselected depth through the feet 12, which can be of the Russian, American, or the depicted Universal design. The micrometer 13 is helpful for less sensitive surgical applications and gross calibration measurements. This setting is generally further fine-tuned with a calibrating microscope to provide closer tolerances for keratotomy procedures.

Figure 3:
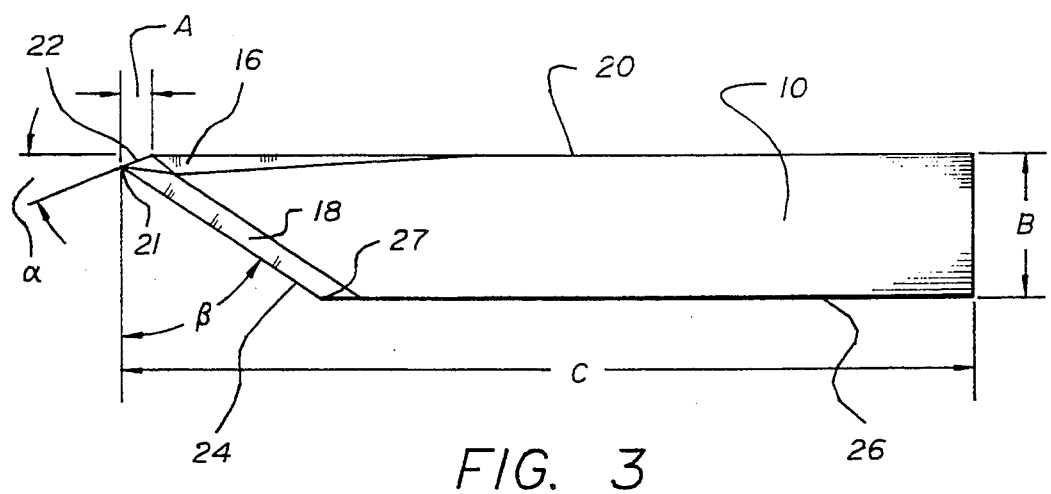
FIGS. 3 and 3a are side plan and partial side plan views of alternative preferred surgical blades of this invention.
Figure 3A:
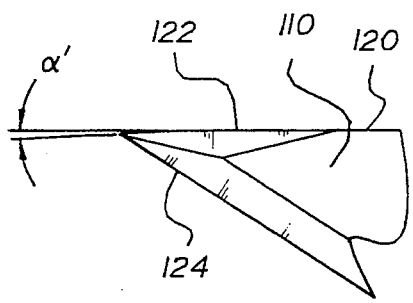
Figure 4:
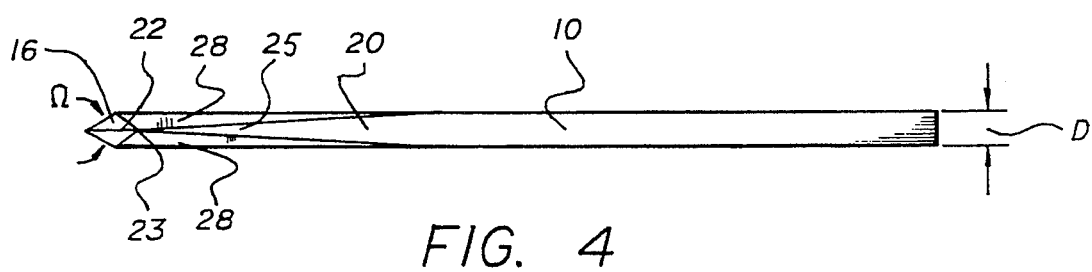
FIG. 4 is a top plan view of the surgical blade of FIG. 3, illustrating the sharpened vertical edge.
Figure 5:
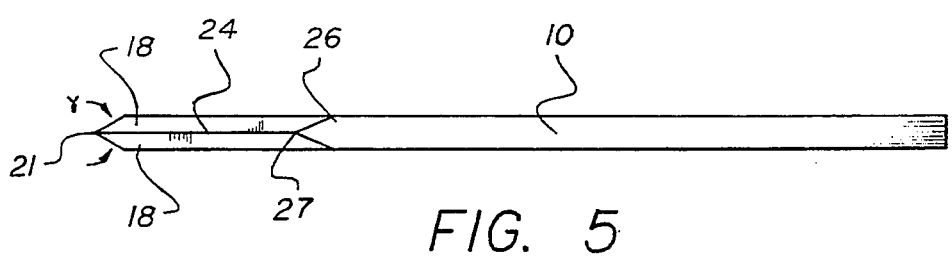
FIG. 5: is a bottom plan view of the surgical blade of FIG. 3, illustrating the angled cutting edge.

In the first preferred blade configuration embodied in FIGS. 3–5, a surgical blade 10 is provided. The blade includes a hard, corrosion resistant material capable of being honed or lapped into a sharp cutting edge. Such materials include stainless steel, glasses, ceramics, and crystalline materials containing natural or synthetic stones, such as diamonds, rubies, sapphires or similar materials of sufficient hardness. Although the term "gemstone" is used, the stones need not be "gem" quality, as industrial quality stones may be sufficient in certain applications. Preferably, however, the gemstone contains a natural diamond of a grade and internal molecular structure suitable for making flat slabs with proper orientation with respect to the cleaving planes. The gemstone is typically provided in a rough shape which is developed by laser cutting or sawing into a generally flat configuration. The more precise facet and cutting edge dimensions are thereafter applied to the diamond slab by cleaving and lapping.

The preferred surgical blade 10 includes a pair of longitudinal sides and a distal end containing first and second cutting edges. The first cutting edge is desirably configured into an angled cutting edge 24 having a leading edge portion 27 and a trailing edge portion 21. The trailing edge portion 21 preferably ends at the distal end portion of the blade 10. The angled cutting edge 24 is provided by a pair of faces or facets 18 which define therebetween an angle $\gamma$. The second cutting edge preferably includes a sharpened vertical edge 22 which forms the distal apex of the blade 10 and tapers proximally along tapered portion 25. The sharpened vertical edge 22 is defined by a pair of faces 16 which form therebetween an angle $\Omega$. (As used herein, the term "vertical" is not limited to an edge which is perpendicular or co-planar with blunt side edge 20 or tapered portion 25, and this term is used generally to provide a comparative orientation with the disclosed angled cutting edges.)

The blunt side edge 20 begins at transition point 23, and extends proximally along the second longitudinal side of the gemstone. The tapered portion 25 is preferably defined by faces or facets 28 having an included angle of about 30°–55°. The tapered portion 25 also presents a substantially blunt surface and may be cut to form a plane, or facet, extending at an angle of about 1°–15°, preferably about 3°–7°, from blunt side edge 20 shown in FIG. 4.

The sharpened vertical edge 22 preferably forms an angle of about +/−90° and more preferably, an acute angle $\alpha$ with the second longitudinal side, and preferably with the blunt side edge 20 or tapered portion 25 of the blade 10. The angled cutting edge 24, on the other hand, forms a preferred acute angle $\beta$ formed with a perpendicular line drawn from the second longitudinal side. The surgical blade 10 further includes a length dimension C, a width dimension B and a thickness D, the preferred ranges of which are described in Table I further in this text.

Alternatively, a blade 110 can be provided with most of the above features, including an angled cutting edge 124 and a blunt side edge 120 situated proximally from a sharpened vertical edge 122, but with a slight taper along the entire vertical edge 122 or most of the vertical edge 122. In this tip variation of the blade configuration of FIG. 3, the vertical edge 122 preferably forms an angle $\alpha'$ of about 1°–15° and more preferably about 3°–7° with the blunt side edge 120, with the faces of the vertical edge 122 and angled cutting edge forming a preferred included angle of about 25°–55°, and more preferably about 33° and 35° respectively.

An alternative preferred surgical blade 30 will now be described with reference to FIGS. 6–9. The alternative surgical blade 30 includes many of the features associated with blade 10, but noticeably includes a recess, having depth measurement I, located along its second longitudinal side. The recess defines a recessed blunt side edge 36 more clearly described in FIG. 9.

Surgical blade 30, as with predecessor blade 10, further includes a sharpened vertical edge 32 which forms a piercing distal tip with angled cutting edge 34 at the distal tip of the blade 30. The blade 30 includes an overall width F, and a recessed portion width H. The overall length of this blade is provided by measurement G, and the thickness of the blade is provided by measurement J. The angled cutting edge 34 has a leading and trailing edge portion similar to that for blade 10, and forms an angle $\beta'$ with a perpendicular line drawn from the sharpened vertical edge 32. The faces of the angled cutting edge 34 form an included angle $\gamma'$, and the faces of the sharpened vertical edge 32 form an included angle $\Omega'$.

Figure 6:
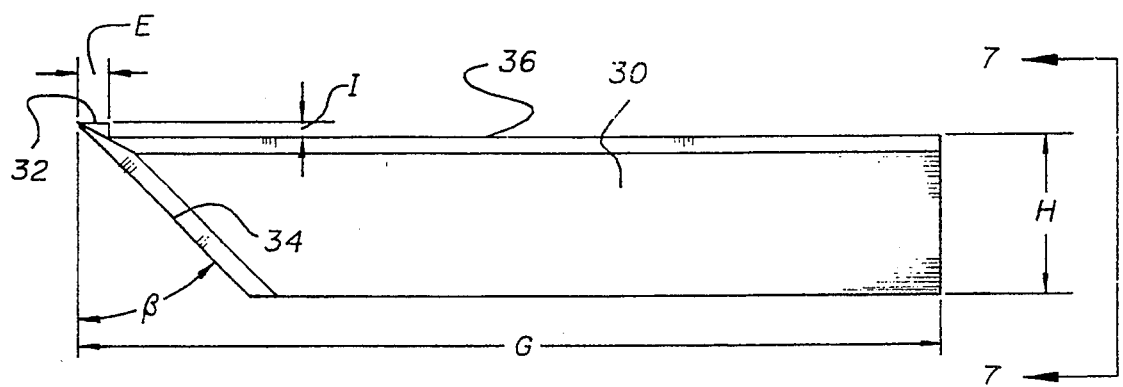
FIGS. 6, 6a, and 6b are side plan and partial side plan views of alternative modified surgical blades of this invention having undercutting capability.
Figures 6A, 6B, 7:
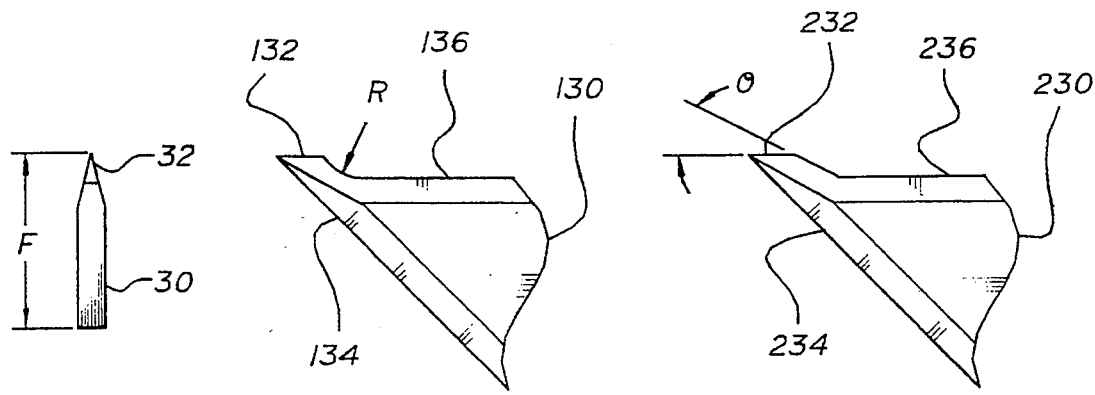
FIG. 7 is an end plan view of the alternative modified surgical blade of FIG. 6.
Figure 8:
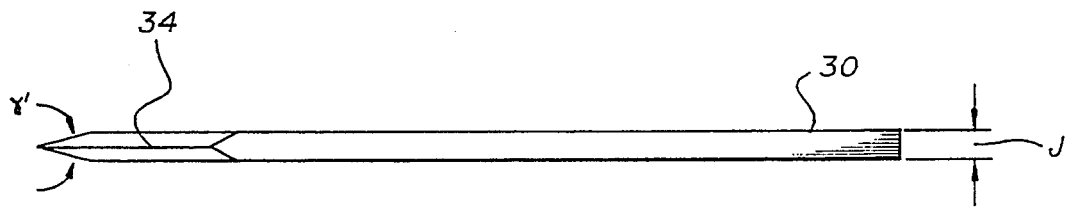
FIG. 8 is a bottom plan view of the alternative modified surgical blade of FIG. 6, illustrating the angled cutting edge.
Figure 9:
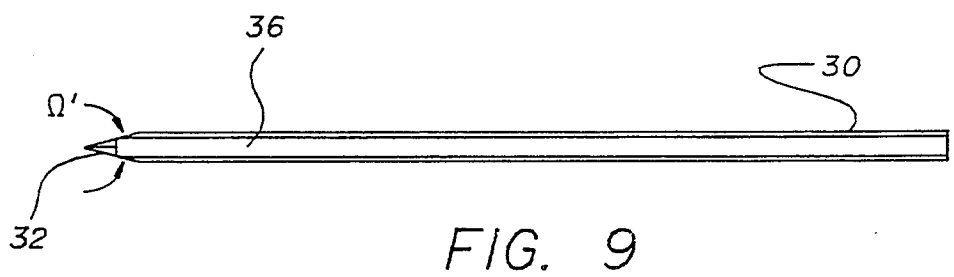
FIG. 9 is a top plan view of the alternative modified surgical blade of FIG. 6, illustrating the sharpened vertical edge and a preferred recessed blunt side edge.

In the further variation of the tip configuration of the blade construction of FIG. 6, a blade 130 can be provided having the similar features of a sharpened vertical edge 132, angled cutting edge 134, and recessed blunt side edge 136. With this particular development, however, a small radius R is provided between the sharpened vertical edge 132 and the recessed blunt side edge 136 to provide a smooth transition between these elements. In practice, this will facilitate! the removal of the knife blade 130 following redeepening of the incision.

In still a further variation of the tip design the blade configuration described in FIG. 6, a blade 230 can be provided with similar features of a sharpened vertical edge 232, angled cutting edge 234, and recessed blunt side edge 236. In this embodiment, a taper is provided between the sharpened vertical edge 232 and the recessed blunt side edge 236. This taper can have an angle $\theta$ of approximately 3°–90°. In both of the embodiments described in FIGS. 6a and b, undercut capability can be provided as with blade 30.

The alternative configurations exhibited by blades 30, 130, and 230 are easier to manufacture since the recessed blunt side edges can be configured with a laser or by conventional sawing and/or grinding methods. The length E of the sharpened vertical edges can thus be more precisely and economically controlled by employing more automated methods, than by the more time-consuming and less accurate lapping wheel procedures employed to configure the cutting facets of blade 10.

Figure 12:
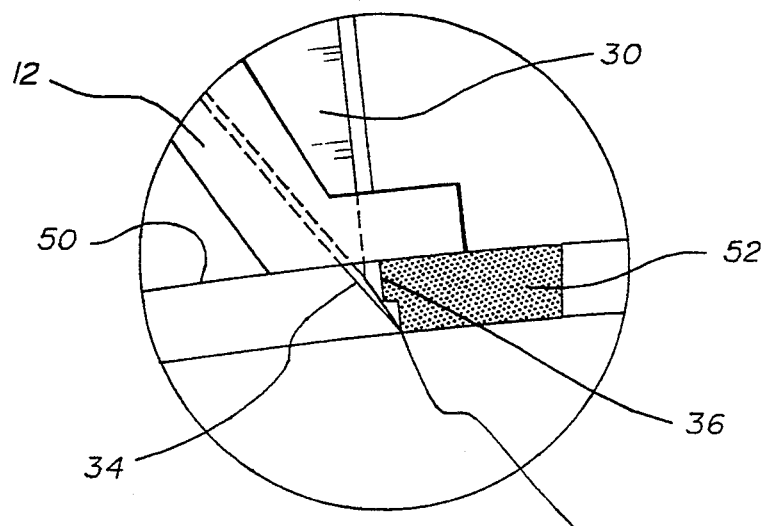
FIG. 12 is an alternative enlarged view of an incision area of a keratotomy procedure including an undercut.

Blades 30, 130, and 230 also provide heretofore unprecedented "undercut" capability, since the projected sharpened vertical edges can be directed beneath the optical zone 52, illustrated in FIG. 12, without creating optical interference or scarring at the surface of optical zone 52. As used herein, the "optical zone" refers to the approximate 2.5–4 mm diameter section of the corneal center, or the corneal region which is immediately above the maximum pupil diameter. Undercutting must be made below the surface of the cornea, since it is believed that this will avoid surface scarring and provide tremendous corrective ability. This observation is based, in part, upon radial keratotomy procedures that have, by erroneous manipulation of the blade, transected the optical zone. It has been determined that these "mistakes" created far more flattening of the cornea than an equivalently sized incision outside the optical zone. The presently described undercutting blades permit nearly perfect perpendicular incisions beneath the surface of the cornea, where glare is less of a problem, and thus, take advantage of the more significant corrective abilities available when flattening occurs in the optical zone itself. The sharpened vertical cutting edges of this invention are "completely" vertical (disposed at about 90° with the corneal surface), or, are less than 15°, preferably less than 8°, and ideally about 3°–7° from being completely vertical, so that they can either cut perpendicularly into the cornea, or be adjusted slightly within the blade holder to provide a vertical cutting edge.

Not only is the recessed blunt side edges of the "undercut" configurations easier to prepare, but the carefully tailored shape of these surfaces provides more resistance to trespassing the original incision point at the optical zone than blade 10, since a more controlled flat rectangular surface is provided. Compare, for example, FIG. 9 with FIG. 4. The tapered portion 25 of blade 10 has very little flat surface area just proximal of the sharpened vertical edge 22. This provides little assurance that the redeepening procedure will terminate at the original incision point. The controlled, large surface area of the recessed blunt side edge 36, on the other hand, provides much more flat surface where it is needed at its most distal portion closest to the sharpened vertical edge 32. This provides a blunter, and less intrusive configuration deeper in the corneal incision. The recessed blunt side edge 36 can be carefully configured by varying the angle $\Omega$ and depth I, to provide a myriad of sharpened vertical edge configurations carefully tailored to provide selected undercut and optical zone resistance capabilities. Preferred dimensional tolerances for the blades 10 and 30 of this invention are provided in Table I below.

TABLE I

| | Preferred Diamond Dimensional Ranges | | | | |
| --- | --- | --- | --- | --- | --- |
| | Genesis | | | Modified | |
| Dimension | Broad | Narrow | Dimension | Broad | Narrow |
| A | .050–.400 mm | .120–.350 mm (.215 mm target) | E | .025–.400 mm | .120–.350 mm (.215 mm target) |
| B | .7–2.5 mm | 1 mm | F | .7–2.0 mm | 1 mm |
| C | 3–8 mm | 6 mm | G | 3–8 mm | 6 mm |
| D | .1–.25 mm | .12 mm | H | .695–1.5 mm | .95 mm |
| $\alpha$ | 1–8° | 3–7° | I | .005–1.5 mm | .05 mm |
| $\beta$ | 25–78° | 45° | J | .1–.25 mm | .12 mm |
| $\Omega$ | 25–45° | 33° | $\beta'$ | 25–78° | 45° |
| $\gamma$ | 30–55° | 45° | $\Omega'$ | 25–45° | 33° |
| | | | $\gamma'$ | 30–55° | 45° |

The preferred surgical blades 10, 110, 30, 130, and 230 of this invention include sharpened vertical edges 22, 122, 32, 132, and 232 and angled cutting edges 24, 124, 34, 134, and 234. The width measurement of the diamond blades B and H and the angles $\beta$ and $\beta'$ are important parameters in determining the depth of the primary incision created by the angled cutting edges during American-style radial keratotomy procedures. The initial radial incisions of an American procedure are about equal to the depth of the exposed angled cutting edge. It can be readily observed that larger cutting angles $\beta$ and $\beta'$ will proportionally increase the cutting depth for a given knife setting and blade width. Accordingly, the depth dimensions A and E for the preferred vertical cutting edges of these blades are designed to lie within the broad range of about 0.05–0.35 mm. The lower limit, 0.05 mm, is defined by the current level of manufacturing ability, and the upper limit is set at a level which will be more than sufficient to "clear up" the remainder of corneal tissue left by typical American technique procedures, but safely beneath the 0.500 mm full corneal thickness. An upper limit of no more than about 400 mm should almost guarantee against superficial scarring.

From a physician's perspective, the lower limit for the vertical edge is desirably no less than about 0.120 mm. This is due to the fact that reverse cutting edges significantly below 0.120 mm require larger $\alpha$ angles which render the vertical cutting edge difficult to maneuver by the surgeon. Vertical cutting edges significantly below 0.120 mm tend to plow rather than cleanly sever the corneal tissue. With such blades, if the operating surgeon does not maintain the blade precisely in the original incision, for example, if the blade is twisted or tilted from the perpendicular, the redeepening procedure may fail to retrace the bottom of the incision, and result in double cuts or additional trauma.

In the American technique, the angles $\beta$ and $\beta'$ generally determine the depth of penetration for the primary incision for any given setting of the surgical blade through the feet 12. It is known, for example, that sharp blades having large $\beta$ angles approaching 78°, or more, can be fabricated with known manufacturing techniques, but such configurations, like blades with a large $\alpha$ measurement, tend to be difficult to maneuver in the cornea. Accordingly, the angled cutting edge is preferably disposed at an angle $\beta$ and $\beta'$ of about 40°–60°. Such cutting edges are capable of severing through approximately 0.400–0.420 mm of the corneal tissue with a 0.500 mm setting. The redeepening procedure for these types of blades would therefore require an exposed vertical edge of something just less than about 0.080–0.100 mm.

Figure 10:
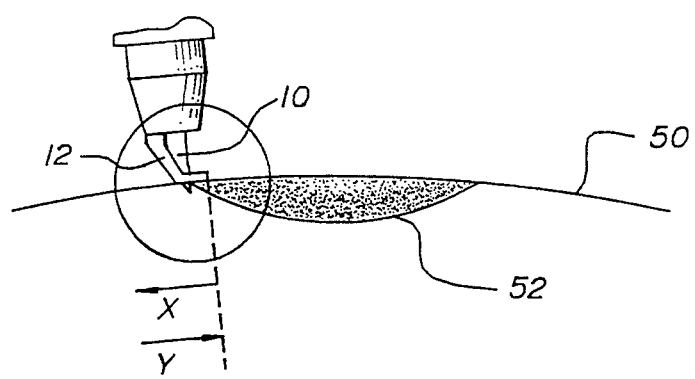
FIG. 10 is a diagrammatic side view of a radial keratotomy procedure.
Figure 11:
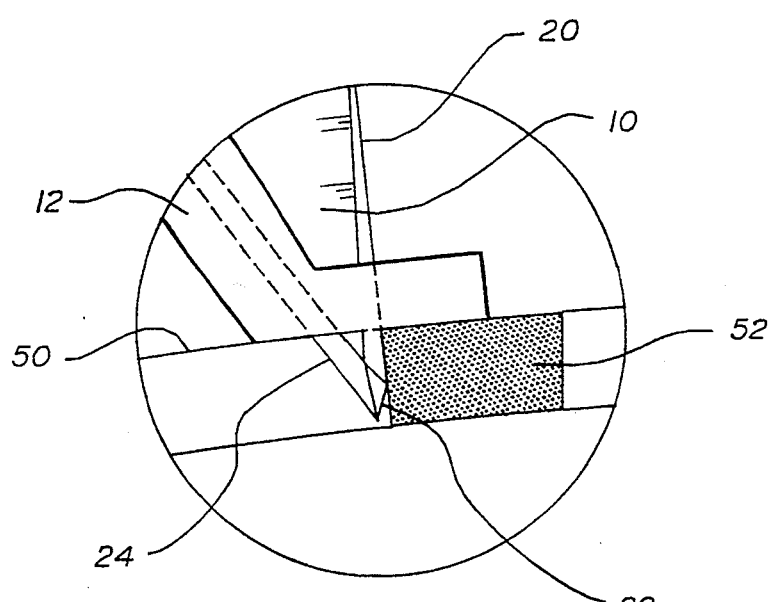
FIG. 11 is an enlarged view of the incision area of the keratotomy procedure illustrated in FIG. 10.

With reference to FIGS. 10–12, preferred keratotomy procedures offered by this invention will now be described. As shown in FIG. 10, the knife blade 10 extending from the preferred universal feet 12 is inserted into the cornea 50, and an initial incision is made starting at the optical zone 52 and cutting toward the limbus of the eye in a first direction X. Without lifting the knife, the incision is retraced in a second direction Y, to redeepen the wound. This provides a uniform incision depth along the entire incision length, unlike the American-style incision. Furthermore, this procedure ensures a more squared-off central or leading edge at the base of the wound enabling not only increased efficacy, but more predictable results as well. The sharpened vertical edge 22 deepens the incision while the blunt side edge 20 prevents intrusion into the optical zone 52 during the retracing of the blade.

As shown in the enlarged view of FIG. 11, the blade 10 is carefully configured so that the sharpened vertical edge 22 of blade 10 does not enter into the optical zone 52. However, in certain keratorefractive surgical procedures, it may be desirable to penetrate the cornea 50 beneath optical zone 52, as shown in FIG. 12. In this application, the sharpened vertical edge 32 of blade 30 becomes a valuable asset. When used in the above-described surgical procedure, sharpened vertical edge 32 will not only provide a redeepening of the wound, but will penetrate beneath the optical zone 52 for a distance equal to the dimension I, (assuming the knife is held substantially perpendicularly with the surface of the cornea 50), wherein contact of the edge of the optical zone 52 with recessed blunt side edge 36 prevents further penetration. This tunnels beneath the optical zone to lengthen the incision at its base, thereby elongating the incision to provide a greater degree of flattening.

From the foregoing, it can be realized that this invention provides improved keratotomy procedures and blades for minimizing optical glare and reducing the possibility of puncturing corneal tissue. Although radial keratotomy procedures are described, this invention would also be suitable for astigmatic and other techniques. The blades of this invention are suitable for use with the American, Russian or combined techniques and provide blade designs suitable for undercutting the optical zone without causing glare. The specific dimensional configurations are approximate measurements only and the disclosed ranges are applicable to all of the disclosed blade configurations, despite the fact that specific ranges are preferred for each blade. Although various embodiments have been illustrated, this was for the purpose of describing, but not limiting the invention. Various modifications, which will become apparent to one skilled in the art, or within the scope of this invention described in the attached claims.

| LIST OF REFERENCE NUMERALS |
| --- |
| 10 Blade |
| 11 Knife Body |
| 12 Feet |
| 13 Micrometer |
| 14 Distal End |
| 16 Sharpened Vertical Edge Face |
| 18 Angled Cutting Edge Face |
| 20 Blunt Side Edge |
| 21 Trailing Edge Portion |
| 22 Sharpened Vertical Edge |
| 23 Transition Point |
| 24 Angled Cutting Edge |
| 25 Tapered Portion |
| 26 Blunt Side Edge |
| 27 Leading Edge Portion |
| 28 Tapered Portion Face |
| 30 Blade |
| 32 Sharpened Vertical Edge |
| 34 Angled Cutting Edge |
| 36 Recessed Blunt Side Edge |
| 50 Cornea |
| 52 Optical Zone |
| 100 Micrometer Surgical Knife |
| 110 Blade |
| 120 Blunt Side Edge |
| 122 Sharpened Vertical Edge |
| 124 Angled Cutting Edge |
| 130 Blade |
| 132 Sharpened Vertical Edge |
| 134 Angled Cutting Edge |
| 136 Recessed Blunt Side Edge |
| 230 Blade |
| 232 Sharpened Vertical Edge |
| 234 Angled Cutting Edge |
| 236 Recessed Blunt Side Edge |

What is claimed is:

1. A surgical knife suitable for use in radial keratotomy procedures, comprising:
an elongated blade having proximal and distal ends, front and back opposing planar surfaces, and first and second longitudinal sides;
said distal end including first and second cutting edges extending distally from said first and second longitudinal sides of said blade, said second cutting edge being shorter than the length of said first cutting edge and having a cutting depth of substantially less than 0.5 mm, wherein said second longitudinal side comprises a blunt side edge portion recess from at least a portion of said second cutting edge and extending distally to a point beyond the proximal end of said first cutting edge.

2. The surgical knife of claim 1, wherein said blade comprises a ruby, diamond, glass or ceramic.

3. The surgical knife of claim 1, wherein said first cutting edge comprises an angled cutting edge having a leading edge portion and a trailing edge portion thereon.

4. The surgical knife of claim 3, wherein said second cutting edge comprises a sharpened edge adjacent to the trailing edge portion of said angled cutting edge.

5. A surgical blade suitable for use in radial keratotomy procedures, comprising:
an elongated diamond having distal and proximal ends, front and back opposing planar surfaces, and first and second substantially parallel longitudinal sides;
said distal end including first and second cutting edges extending distally from said first and second longitudinal sides of said diamond and joined to form an acute angle terminating with a sharp apex for piercing into a cornea, said second cutting edge being shorter than the length of said first cutting edge and having a cutting depth of less than about 0.350 mm;
said second longitudinal side containing a blunt surface comprising a portion of said second longitudinal side recessed from at least a portion of said cutting edge and located proximally from said second cutting edge, said blunt surface extending distally to a point beyond the proximal end of said first cutting edge.

6. The surgical blade of claim 5, wherein said elongated diamond comprises a length of about 3–8 mm and a width of about 0.7–1.5 mm.

7. A surgical knife suitable for use in radial keratotomy procedures, comprising:
an elongated crystalline gemstone blade having proximal and distal ends, front and back opposing planar surfaces, and first and second longitudinal sides, said distal end including first and second cutting edges extending distally from said first and second longitudinal sides of said gemstone, said second cutting edge being shorter than the length of said first cutting edge and having a cutting depth of less than about 0.350 mm, wherein said second longitudinal side comprises a blunt side edge portion recessed from at least a portion of said second cutting edge and extending distally to a point beyond the proximal end of said first cutting edge; and
a blade holder for securing said blade, said blade holder sized to fit into a surgeon's hand and including a foot portion for contacting and gliding over a peripheral portion of said cornea, while helping to maintain said blade at a preselected incision depth.

8. A radial keratotomy procedure for correcting a refractive error in the focussing of light through the optical zone of a cornea, comprising:
providing a surgical knife including an elongated crystalline gemstone blade having proximal and distal ends, front and back opposing planar surfaces, and first and second longitudinal sides, said distal end including first and second cutting edges extending distally from said first and second longitudinal sides of said gemstone blade and joined to form a sharp apex for piercing into said cornea, said second cutting edge being shorter than the length of said first cutting edge and having a cutting depth of substantially less than 500 $\mu$, wherein said second longitudinal side comprises a blunt side edge portion recessed from at least a portion of said second cutting edge and extending distally to a point beyond the proximal end of said first cutting edge;
piercing into said cornea with said sharp apex and slicing radially outwardly from about said optical zone with said first cutting edge to form a first incision; and
retracing a bottom portion of said first incision with said second cutting edge to deepen said incision without puncturing said cornea or significantly optically interfering with said optical zone.

9. A surgical knife suitable for use in radial keratotomy procedures, comprising:

an elongated blade having proximal and distal ends, front and back opposing planar surfaces, and first and second longitudinal sides;

said distal end including first and second cutting edges extending distally from said first and second longitudinal sides of said blade, said second cutting edge being substantially shorter than 500 μ and the length of said first cutting edge and having a cutting depth of at least about 0.120 mm, wherein said second longitudinal side comprises a blunt side edge portion recessed from at least a portion of said second cutting edge and extending distally to a point beyond the proximal end of said first cutting edge.

10. The surgical knife of claim 9, wherein said blade comprises stainless steel, a ruby, diamond, glass or ceramic.

11. The surgical knife of claim 9, wherein said first cutting edge comprises an angled cutting edge having a leading edge portion and a trailing edge portion thereon.

12. The surgical knife of claim 11, wherein said second cutting edge comprises a sharpened edge adjacent to the trailing edge portion of said angled cutting edge.

13. The surgical knife of claim 12, wherein said sharpened edge comprises a cutting depth of less than about 0.400 mm.

14. A surgical blade suitable for use in radial keratotomy procedures, comprising:

an elongated diamond having distal and proximal ends, front and back opposing planar surfaces, and first and second substantially parallel longitudinal sides;

said distal end including first and second cutting edges extending distally from said first and second longitudinal sides of said diamond and joined to form an acute angle terminating with a sharp apex for piercing into a cornea, said second cutting edge being shorter than the length of said first cutting edge and having a cutting depth of about 0.120–0.350 mm;

said second longitudinal side containing a blunt surface located recessed from at least a portion of said cutting edge and proximally from said second cutting edge, said blunt surface extending distally to a point beyond the proximal end of said first cutting edge.

15. The surgical blade of claim 14, wherein said first cutting edge comprises an angled cutting edge having a pair of edge faces forming an angle of about 30°–55°.

16. The surgical blade of claim 14, wherein said second cutting edge comprises a sharpened edge having a pair of faces which form an included angle of about 25°–45°.

17. The surgical blade of claim 14, wherein said elongated diamond comprises a length of about 3–8 mm and a width of about 0.7–1.5 mm.

18. A surgical blade suitable for producing an undercut in the optical zone during radial keratotomy procedures, comprising:

an elongated crystalline gemstone having proximal and distal ends, front and back opposing planar surfaces, and first and second longitudinal sides;

said distal end including first and second cutting edges extending distally from said first and second longitudinal sides of said gemstone and joined to form a sharp apex for piercing into a cornea, said second cutting edge being shorter than the length of said first cutting edge and having a cutting depth of about 0.120–0.350 mm, said second cutting edge including a portion that projects laterally from said second longitudinal side, said second longitudinal side containing a blunt surface recessed from at least a portion of said cutting edge and located proximally from said second cutting edge for minimizing penetration in to an optical zone during said keratotomy procedures, said blunt surface extending distally to a point beyond the proximal end of said first cutting edge.

19. A surgical knife suitable for use in radial keratotomy procedures, comprising:

an elongated blade mounted within a holder, said blade having proximal and distal ends, front and back opposing planar surfaces, and first anti second longitudinal sides;

said distal end including at least a first cutting edge having a depth of about 120–350 microns and a blunt side edge portion recessed from at least a portion of said cutting edge and located proximally from said first cutting edge;

said first cutting edge and said recessed blunt side edge portion being capable of penetrating into a corneal tissue so that said first cutting edge incises beneath an optical zone of an eye without generating surface scarring.

20. The surgical knife of claim 19, wherein said first cutting edge is capable of penetrating as much as 0.05 mm beneath the optical zone without surface scarring.

21. The surgical knife of claim 20, wherein said first cutting edge is capable of providing a correction of more than about 6–12 diopters during said keratotomy procedures.

* * * * *